(12) United States Patent
Massimini et al.

(10) Patent No.: US 11,950,799 B2
(45) Date of Patent: *Apr. 9, 2024

(54) PROPULSION SYSTEM FOR INERTIAL ENERGY TRANSFER TO DISRUPT VASCULAR LESIONS

(71) Applicant: Boston Scientific Scimed, Inc., Maple Grove, MN (US)

(72) Inventors: Daniel Frank Massimini, Brooklyn Park, MN (US); Roger W. McGowan, Otsego, MN (US); Christopher Smuk, Champlin, MN (US); Binh C. Tran, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 43 days.

This patent is subject to a terminal disclaimer.

(21) Appl. No.: 17/847,874

(22) Filed: Jun. 23, 2022

(65) Prior Publication Data

US 2022/0313304 A1 Oct. 6, 2022

Related U.S. Application Data

(63) Continuation of application No. 16/909,687, filed on Jun. 23, 2020, now Pat. No. 11,399,862.
(Continued)

(51) Int. Cl.
*A61B 17/3203* (2006.01)
*A61B 17/22* (2006.01)

(52) U.S. Cl.
CPC ............. *A61B 17/32037* (2013.01); *A61B 2017/22051* (2013.01)

(58) Field of Classification Search
CPC ............. A61B 17/22; A61B 17/22012; A61B 17/32037; A61B 2017/22025;
(Continued)

(56) References Cited

U.S. PATENT DOCUMENTS

| 5,030,227 A | 7/1991 | Rosenbluth et al. |
| 5,154,347 A | 10/1992 | Vijay |

(Continued)

FOREIGN PATENT DOCUMENTS

| WO | 2018194894 | 10/2018 |

OTHER PUBLICATIONS

"AngioJet Ultra Thrombectomy System," Bayer Healthcare AngioJet Ultra Brochure, 2013 (5 pages).
(Continued)

*Primary Examiner* — Jocelin C Tanner
(74) *Attorney, Agent, or Firm* — Pauly, DeVries Smith & Deffner LLC

(57) ABSTRACT

Embodiments herein relate to systems and methods for intravascular lesion disruption. In an embodiment, a catheter system for imparting pressure to induce fractures upon a vascular lesion within or adjacent a blood vessel wall is included. The system includes a catheter configured to advance to a vascular lesion, the catheter including an elongate shaft that defines at least a first orifice for fluid flow; a balloon, coupled to the elongate shaft, that surrounds the first orifice where the balloon can expand from a collapsed configuration suitable for advancing the catheter through a patient's vasculature to a first expanded configuration suitable for anchoring the catheter in position relative to a treatment site; and a propulsion system configured to propel a fluid from the first orifice toward the balloon wall to create an inertial impulse in a vessel wall to transfer momentum to the vascular lesion. Other embodiments are also included herein.

20 Claims, 13 Drawing Sheets

Related U.S. Application Data

(60) Provisional application No. 62/865,379, filed on Jun. 24, 2019.

(58) Field of Classification Search
CPC .......... A61B 2017/22051; A61B 2017/22061; A61M 25/10185; A61M 25/104; A61M 2025/109

See application file for complete search history.

(56) References Cited

U.S. PATENT DOCUMENTS

| | | | |
|---|---|---|---|
| 7,344,528 B1 | 3/2008 | Tu et al. | |
| 8,574,247 B2 | 11/2013 | Adams et al. | |
| 8,709,075 B2 | 4/2014 | Adams et al. | |
| 8,728,091 B2 | 5/2014 | Hakala et al. | |
| 8,747,416 B2 | 6/2014 | Hakala et al. | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,044,618 B2 | 6/2015 | Hawkins et al. | |
| 9,072,534 B2 | 7/2015 | Adams et al. | |
| 9,180,280 B2 | 11/2015 | Hawkins et al. | |
| 11,399,862 B2 * | 8/2022 | Massimini | A61B 17/22012 |
| 2005/0197668 A1 | 9/2005 | Lim et al. | |
| 2006/0205992 A1 | 9/2006 | Lubock et al. | |
| 2010/0056865 A1 | 3/2010 | Nagamachi et al. | |
| 2011/0152683 A1 | 6/2011 | Gerrans et al. | |
| 2012/0226230 A1 * | 9/2012 | Gerrans | A61B 5/4839 604/103.01 |
| 2018/0304053 A1 | 10/2018 | Eggert et al. | |
| 2020/0046946 A1 | 2/2020 | Staley et al. | |
| 2020/0046949 A1 | 2/2020 | Chisena et al. | |
| 2020/0397461 A1 | 12/2020 | Massimini et al. | |

OTHER PUBLICATIONS

File History for U.S. Appl. No. 16/909,687 downloaded Jul. 27, 2022 (244 pages).

"Hydrostatic Shock," Wikipedia article retrieved from URL <https://en.wikipedia.org/w/index.php?title=Hydrostatic_shock&oldid=993317318> at least as early as Jun. 5, 2020 (13 pages).

"The Dangers of Water Hammer and How to Prevent It," Entex Technolgies, Ripples Blog post Apr. 23, 2015, retrieved from <https://www.entexinc.com/the-dangers-of-water-hammer-and-how-to-prevent-it/>.

"Water Hammer Introduction," revised by Rick Sellens Feb. 26, 1996. Retrieved from URL <http://sellensr.me.queensu.ca/sellens/451/hammer.htm> (1 page).

"Water Hammer," Wikipedia article retrieved from URL <https://en.wikipedia.org/w/index.php?title=Water_hammer&oldid=993665593"> published at least as early as Feb. 14, 2019 (12 pages).

"What is Water Hammer?," White Paper published by Baker Corp. at least as early as Apr. 23, 2015 (4 pages).

Dvorsky, Richard, et al. "Pulsed Water Jet Generated by Pulse Multiplication," Tehnicki vjesnik 23, 4(2016), 959-967 (10 pages).

Rinfret, Stephane, et al. "Effectiveness of Rheolytic Coronary Thrombectomy With the AngioJet Catheter," The American Journal of Cardiology vol. 90, Sep. 1, 2002 470-476 (7 pages).

Versluis, Michel, et al. "How Snapping Shrimp Snap: Through Cavitating Bubbles," Science 289 (5487), 2114-2117 (5 pages).

Watanabe, Hiroki, et al. "A Prototype Apparatus for Microexplosion Cystolithotripsy," Tohoku. J. exp. Med., 1980, 132, 243-244 (2 pages).

\* cited by examiner

PROPULSION SYSTEM FOR INERTIAL ENERGY TRANSFER TO DISRUPT VASCULAR LESIONS

This application is a continuation of U.S. patent application Ser. No. 16/909,687 filed Jun. 23, 2020, which claims the benefit of U.S. Provisional Application No. 62/865,379 filed Jun. 24, 2019, the content of which is herein incorporated by reference in its entirety.

FIELD

Embodiments herein relate to systems and methods for utilizing a propulsion system for intravascular lesion disruption. More specifically, embodiments herein relate to utilizing a propulsion system for the generation of one or more fluid jets for intravascular lesion disruption within a blood vessel.

BACKGROUND

Vascular lesions within vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

SUMMARY

In a first aspect, a catheter system for imparting pressure to induce fractures upon a vascular lesion within or adjacent a vessel wall of a blood vessel, is included. The catheter system can include a catheter configured to advance to a vascular lesion location within the blood vessel, where the catheter is included having an elongate shaft. The elongate shaft defines at least a first orifice for fluid flow. The catheter can include a balloon coupled to the elongate shaft and surrounding the first orifice, the balloon having a balloon wall and configured to expand from a collapsed configuration suitable for advancing the catheter through a patient's vasculature to a first expanded configuration suitable for anchoring the catheter in position relative to a treatment site. The catheter system can include a propulsion system configured to, when the balloon wall is in contact with the vessel wall, propel a fluid from the first orifice toward the balloon wall to create an inertial impulse in a vessel wall to transfer momentum to the vascular lesion.

In a second aspect, in addition to one or more of the preceding or following aspects, or in the alternative to some aspects, the fluid is propelled toward the balloon wall at a velocity can include a minimum of 1 meters per second (m/s), 5 m/s, or 10 m/s, where the velocity is measured where a fluid jet exits from the first orifice.

In a third aspect, in addition to one or more of the preceding or following aspects, or in the alternative to some aspects, the elongate shaft defines at least two orifices, at least three orifices, or at least four orifices from which fluid is propelled within the balloon toward the balloon wall.

In a fourth aspect, in addition to one or more of the preceding or following aspects, or in the alternative to some aspects, the orifices defined in the elongate shaft are spaced around a diameter of the elongate shaft, are spaced along a length of the elongate shaft, or both.

In a fifth aspect, in addition to one or more of the preceding or following aspects, or in the alternative to some aspects, the elongate shaft further defines a propulsion fluid lumen, where the propulsion system further includes an external fluid flow source in fluid communication with a proximal region of the propulsion fluid lumen and an actuation valve at a distal region of the propulsion fluid lumen configured to create a pulsed fluid jet propelled from the first orifice.

In a sixth aspect, in addition to one or more of the preceding or following aspects, or in the alternative to some aspects, where the actuation valve includes an electromechanical valve and a control wire extending along the elongate shaft, or a rotary mechanical valve and a rotary control shaft extending along the elongate shaft.

In a seventh aspect, in addition to one or more of the preceding or following aspects, or in the alternative to some aspects, the propulsion system further includes: a piston located within a piston lumen defined by the elongate shaft at a distal region of the elongate shaft, and a mechanical spring configured to accelerate the piston to propel fluid from the first orifice.

In an eighth aspect, in addition to one or more of the preceding or following aspects, or in the alternative to some aspects, the mechanical spring is located at a distal region of the elongate shaft or where the mechanical spring is located at a proximal region of the elongate shaft.

In a ninth aspect, in addition to one or more of the preceding or following aspects, or in the alternative to some aspects, the propulsion system includes a piston within a piston lumen defined by the elongate shaft at a distal region of the elongate shaft and an electromagnet surrounding the piston lumen, where the electromagnet is configured to be energized to accelerate the piston along the piston lumen causing fluid to be propelled from the first orifice.

In a tenth aspect, in addition to one or more of the preceding or following aspects, or in the alternative to some aspects, the electromagnet is configured to be energized to accelerate the piston back and forth between a proximal region of the piston lumen and a distal region of the piston lumen.

In an eleventh aspect, in addition to one or more of the preceding or following aspects, or in the alternative to some aspects, the elongate shaft defines the first orifice and a second orifice at a proximal region of the piston lumen within the balloon and further defines a third orifice and a fourth orifice at a distal region of the piston lumen within the balloon.

In a twelfth aspect, in addition to one or more of the preceding or following aspects, or in the alternative to some aspects, the propulsion system includes explosive charges located within the elongate shaft, where the explosive charges are configured to rapidly accelerate fluid from at least the first orifice within the balloon toward the balloon wall.

In a thirteenth aspect, a method for generating pressure to induce fractures upon a vascular lesion within or adjacent a vessel wall of a blood vessel, is included. The method can include advancing a catheter to a vascular lesion location within the blood vessel, where the catheter can include a balloon coupled to an elongate shaft. The method can include expanding the balloon from a collapsed configuration suitable for advancing the catheter through a patient's vasculature to a first expanded configuration suitable for anchoring the catheter in position relative to the vascular lesion location. The method can include after expanding the balloon, propelling a fluid from a first orifice defined in the elongate shaft toward a balloon wall, thereby imparting pressure upon the vascular lesion to induce fractures in the vascular lesion.

In a fourteenth aspect, in addition to one or more of the preceding or following aspects, or in the alternative to some aspects, the method can further include, after propelling the fluid, further inflating the balloon to a second further expanded configuration.

In a fifteenth aspect, in addition to one or more of the preceding or following aspects, or in the alternative to some aspects, where propelling the fluid further includes propelling the fluid toward the balloon wall at a velocity can include a minimum of 1 meters per second (m/s), 5 m/s, or 10 m/s, where the velocity is measured where a fluid jet exits from the first orifice.

In a sixteenth aspect, in addition to one or more of the preceding or following aspects, or in the alternative to some aspects, where propelling the fluid further includes operating an actuation valve located at a distal region of a propulsion fluid lumen defined in the elongate shaft to pulse the fluid and create a pulsed jet of fluid.

In a seventeenth aspect, in addition to one or more of the preceding or following aspects, or in the alternative to some aspects, where the actuation valve is an electromechanical actuation valve and activating the actuation valve includes applying a voltage to a control wire extending along the elongate shaft.

In an eighteenth aspect, a catheter system for imparting pressure to induce fractures upon a vascular lesion within or adjacent a vessel wall of a blood vessel, is included. The catheter system can include a catheter configured to advance to a vascular lesion location within the blood vessel, where the catheter can include an elongate shaft. The elongate shaft defines at least a first orifice and a second orifice for fluid flow, where the first orifice and second orifice are spaced from each other circumferentially, and where the elongate shaft further defines a propulsion fluid lumen. The catheter system can include a balloon coupled to the elongate shaft and surrounding the first orifice and second orifice. The balloon can have a balloon wall and be configured to expand from a collapsed configuration suitable for advancing the catheter through a patient's vasculature to a first expanded configuration suitable for anchoring the catheter in position relative to a treatment site. The catheter system can include a propulsion system that can include an external fluid flow source in fluid communication with a proximal end of the propulsion fluid lumen and an actuation valve at a distal end of the propulsion fluid lumen. The propulsion system can be configured to, when the balloon wall is in contact with the vessel wall, propel a pulsed jet of fluid propelled from the first orifice and from the second orifice toward the balloon wall to create an inertial impulse in a vessel wall to transfer momentum to the vascular lesion.

In a nineteenth aspect, in addition to one or more of the preceding or following aspects, or in the alternative to some aspects, the pulsed jet of fluid can be propelled toward the balloon wall at a velocity can include a minimum of 1 meters per second (m/s), 5 m/s, or 10 m/s where the velocity is measured where a fluid jet exits from the first orifice.

In a twentieth aspect, in addition to one or more of the preceding or following aspects, or in the alternative to some aspects, where the actuation valve includes an electromechanical valve and a control wire extending along the elongate shaft, or a rotary mechanical valve and a rotary control shaft extending along the elongate shaft.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Treatment of vascular lesions can reduce major adverse events or death in affected subjects. A major adverse event is one that can occur anywhere within the body due to the presence of a vascular lesion. Major adverse events can include, but are not limited to major adverse cardiac events, major adverse events in the peripheral or central vasculature, major adverse events in the brain, major adverse events in the musculature, or major adverse events in any of the internal organs.

The systems and methods disclosed herein describe the use of a catheter system including a propulsion system for intravascular lesion disruption. In various embodiments herein, the catheter systems herein are configured to propel a fluid jet toward a balloon wall to create an inertial impulse in a vessel wall to transfer momentum to a vascular lesion. The catheter systems are adapted to propel a fluid jet toward a balloon wall at a minimum velocity of 1 meters per second (m/s), 5 m/s, or 10 m/s, where the velocity of the fluid is measured where a fluid jet exits from the first orifice.

Without being bound by any particular theory, it will be appreciated that as a fluid jet travels rapidly towards a solid object, such as a treatment site within or adjacent to the vasculature of a patient, upon impact at that treatment site a hydraulic shock will result as the fluid changes momentum upon impact with the treatment site. The force of the impact can fracture and disrupt a vascular lesion at the treatment site.

As used herein, the terms "intravascular lesion" or "vascular lesion", can be used interchangeably, and describe any lesion region within or adjacent to a vessel wall. Examples of vascular lesions include calcified vascular lesions and fibrous vascular lesions.

Figure 1:
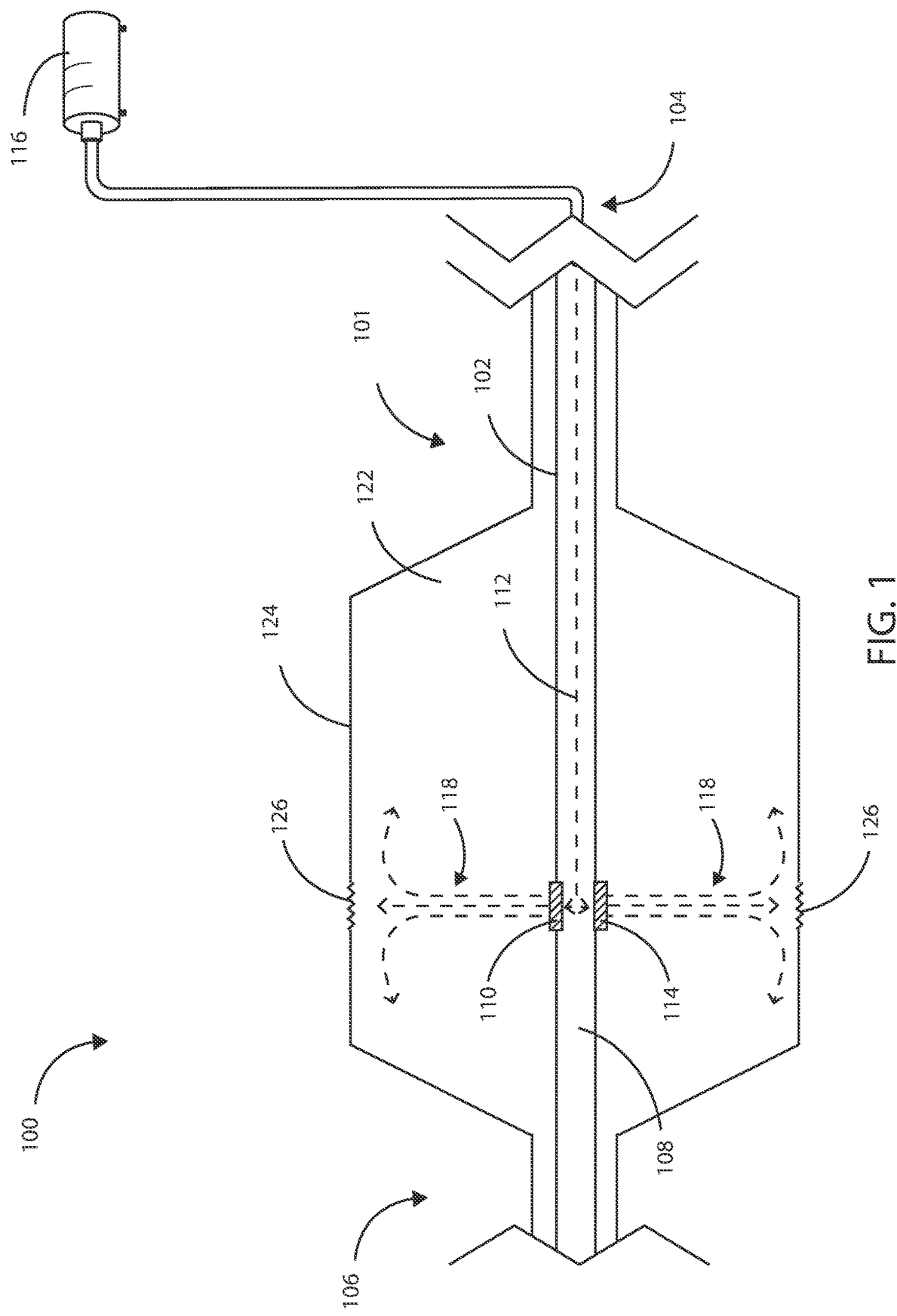
FIG. 1 is a schematic cross-sectional view of a catheter system in accordance with various embodiments herein.

It will be appreciated that the catheter systems herein can include many different forms. Referring now to FIG. 1, a schematic cross-sectional view of a catheter system 100 is shown in accordance with various embodiments herein. Catheter system 100 can be adapted for imparting pressure to induce fractures upon a vascular lesion within or adjacent a vessel wall of a blood vessel. In some embodiments, the vascular lesion can include a calcified vascular lesion. In some embodiments, the vascular lesion can include a fibrous lesion.

The catheter system 100 can include a catheter 101 configured to advance to a vascular lesion location within a blood vessel. The catheter 101 can have an elongate shaft 102 extending from a proximal region 104 to a distal region 106 and can also include a lumen 108. The elongate shaft 102 can include at least a first orifice 110 for fluid flow 112. Fluid flow 112 can direct fluid through at least the first orifice 110 such that a fluid jet 118 exits from the first orifice 110. In some embodiments, the elongate shaft 102 can include a second orifice 114 for fluid flow 112. In some embodiments, the catheter 101 can have a distal end opening and can accommodate and be tracked over a guide wire to a treatment location. In some embodiments, the elongate shaft defines at least two orifices, at least three orifices, or at least four orifices from which fluid is propelled within the balloon toward the balloon wall. In some embodiments, the elongate shaft defines more than four orifices.

The catheter system 100 includes a balloon 122 coupled to the elongate shaft 102 of the catheter 101 and surrounding the first orifice 110. The balloon 122 has a balloon wall 124 and can expand from a collapsed configuration suitable for advancing the catheter 101 through a patient's vasculature to a first expanded configuration suitable for anchoring the catheter 101 in position relative to a treatment site. In some embodiments, the balloon 122 can be further inflated to a second expanded configuration. Expansion of the balloons herein to various expanded configurations will be discussed in more detail in reference to the methods described below.

The catheter system 100 includes a propulsion system configured to, when the balloon wall 124 is in contact with a vessel wall, propel a fluid from the first orifice 110 toward the balloon wall 124 to create an inertial impulse 126 in a vessel wall to transfer momentum to a vascular lesion. The propulsion system is the group of elements, some internal and some external, that are configured to work together to propel the fluid toward the balloon wall, including, for example, an external fluid flow source 116. The external fluid flow source 116 can provide a flow of pressurized fluid. The propulsion system can include an external, pulsed, fluid source capable of providing a high-pressure pulsed fluid jet through the first orifice 110 in the balloon. The external fluid flow source 116 can include a control system and an actuator valve to create a pulsed fluid source.

Exemplary fluids can include water, saline, contrast medium, or any combination thereof. One example of a balloon fluid is a composition of 50% saline and 50% contrast medium. The fluid jet can be propelled toward the balloon wall at a minimum velocity of 1 meters per second (m/s), 5 m/s, or 10 m/s, where the velocity is measured where a fluid jet exits from the first orifice. In some embodiments, the velocity of the fluid jet being propelled from each orifice can be greater than or equal to 1 m/s, 5 m/s, 10 m/s, 20 m/s, 30 m/s, 40 m/s, 50 m/s, 60 m/s, 70 m/s, 80 m/s, 90 m/s, 100 m/s, 110 m/s, 120 m/s, 130 m/s, 140 m/s, 150 m/s, 160 m/s, 170 m/s, 180 m/s, 190 m/s, 200 m/s, 210 m/s, 220 m/s, 230 m/s, 240 m/s, or 250 m/s, or can be an amount falling within a range between any of the foregoing.

Figure 2:
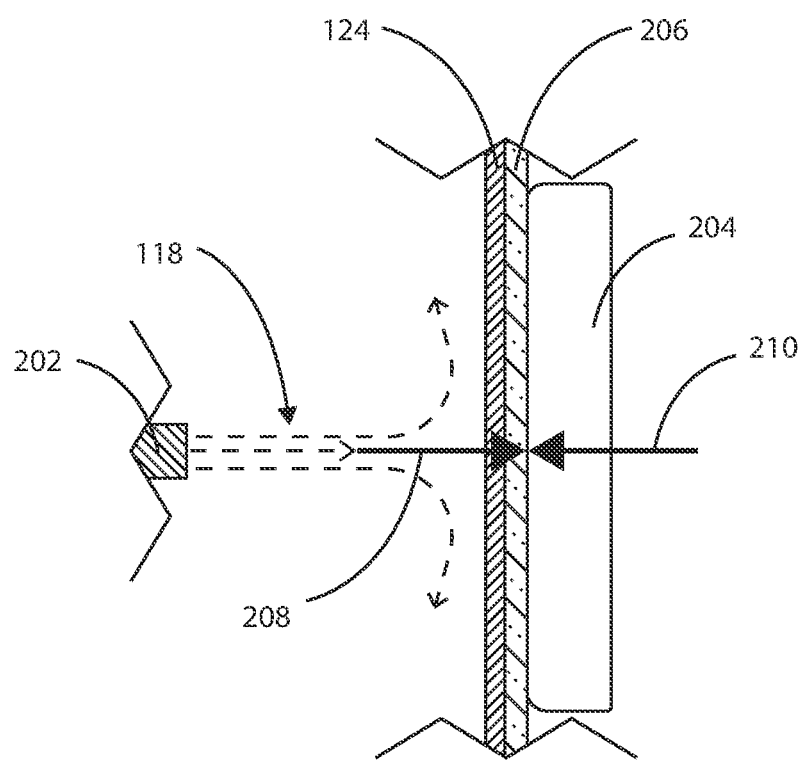
FIG. 2 is a schematic view of a fluid jet in accordance with various embodiments herein.

The fluid jets of the catheter systems described herein can disrupt a vascular lesion within or adjacent to a vessel of a patient. Referring now to FIG. 2, a schematic view of a fluid jet 118 is shown in accordance with various embodiments herein. Fluid jet 118 can be generated by the flow of a fluid from the orifice 202 toward the balloon wall 124 to create an inertial impulse in a vessel wall 206 to transfer momentum to the vascular lesion 204 to result in the disruption the vascular lesion 204. The force 208 exerted on the vessel wall 206 is equal to the force 210 experienced by the vascular lesion 204.

Without wishing to be bound by any particular theory, it is believed that a fluid jet created by a non-compressible fluid having a velocity, v, such as those fluids described herein, can exert an inertial impulse on a vessel wall that can transfer momentum from the fluid jet to the vascular lesion within or adjacent to a vessel wall. Momentum, p, of an object is a vector quantity that describes the resistance of an object in motion to stopping, and it can be defined as the mass, m, of the object times the velocity, v, of the object, or p=m·v. The impulse, J, experienced by an object is a vector quantity that describes the effect of a force, F, acting on an object over a period of time, t, or J=F·t. Momentum and impulse in a system are related via the Impulse-Momentum Theorem which provides that the change in momentum of an object equals the impulse applied to it. Thus, in a closed system where mass is conserved, momentum and impulse are related by the following equation:

$$J=\Delta p=m\Delta v=F\Delta t$$

The fluid jet having a velocity v changes direction when it encounters the balloon wall which is obstructed from further expansion by a lesion in a vessel wall. The change in momentum (impulse) of the fluid jet results in a fracture force to the lesion in the vessel wall.

Orifice Configurations (FIGS. 3-8)

Figure 3:
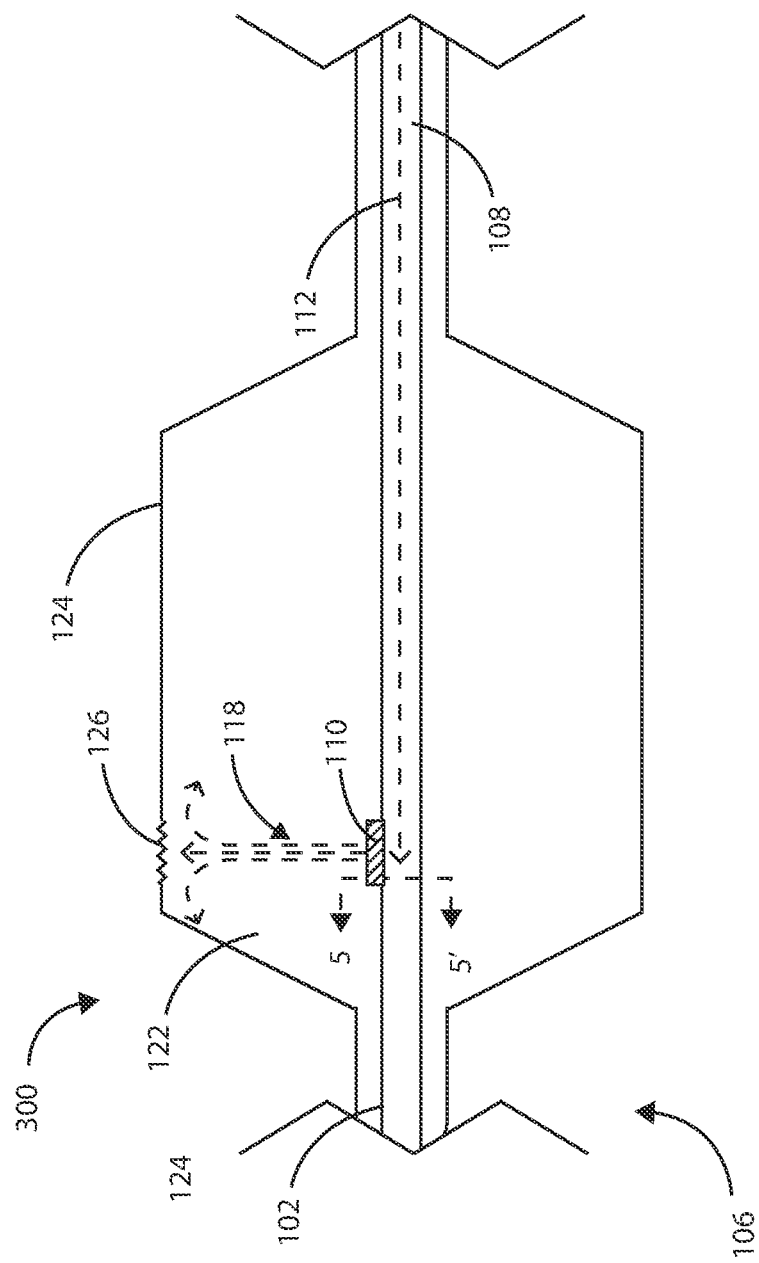
FIG. 3 is a schematic cross-sectional view of a catheter system in accordance with various embodiments herein.
Figure 4:
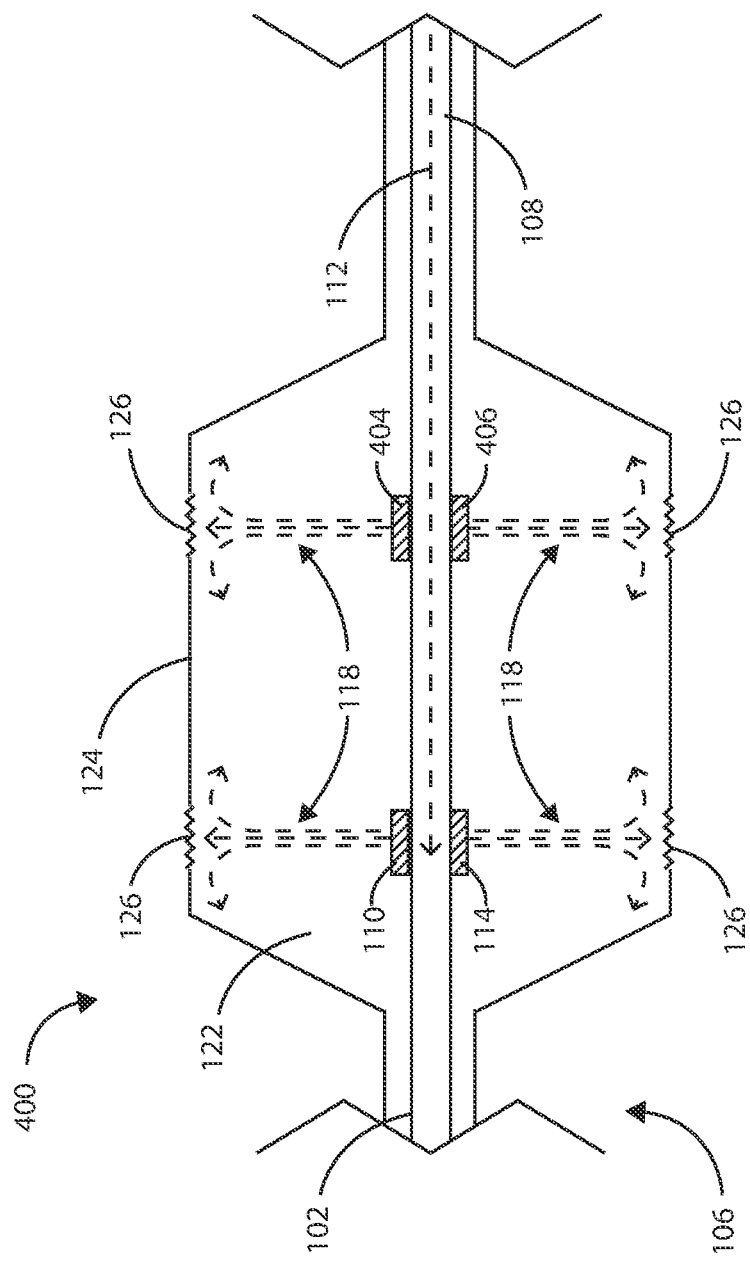
FIG. 4 is a schematic cross-sectional view of a catheter system in accordance with various embodiments herein.

It will be appreciated that the catheters herein can include one or more orifices. Catheters can include one orifice, as shown in FIG. 3, can include two orifices, as shown in FIG. 1, can include four orifices as shown in FIG. 4, or can include a variety of different numbers of and configurations of orifices. When an orifice is described herein, any type of opening or discharge mechanism can be present in the particular embodiment, such as a port or nozzle.

Referring now to FIGS. 3 and 4, schematic cross-sectional views of catheters 300 and 400 are shown in accordance with various embodiments herein. In the configuration shown in FIG. 3, catheter 300 includes balloon 122 having a balloon wall 124. The catheter can include an elongate shaft 102 extending from a proximal region to a distal region 106 and can also include a lumen 108. The elongate shaft 102 can include a first orifice 110 and a fluid flow 112. Fluid flow 112 can direct fluid through the first orifice 110 such that a fluid jet 118 exits from the first orifice 110 toward the balloon wall 124 and creates an inertial impulse 126 at the balloon wall 124.

In the configuration shown in FIG. 4, catheter 400 includes balloon 122 having a balloon wall 124. The catheter can include an elongate shaft 102 extending from a proximal region to a distal region 106 and can also include a lumen 108. The elongate shaft 102 can include a first orifice 110, a second orifice 114, a third orifice 404, and a fourth orifice 406 and a fluid flow 112. Fluid flow 112 can direct fluid through the first, second, third, and fourth orifices 110, 114, 404, and 406, respectively, such that a fluid jet 118 exits from each orifice toward the balloon wall 124 and creates an inertial impulse 126 at the balloon wall 124. In FIG. 4, first orifice 110 and second orifice 114 are radially spaced from each other by about 180 degrees and are located at the same longitudinal position as each other along the elongate shaft 102. In FIG. 4, third orifice 404 and fourth orifice 406 are radially spaced from each other by about 180 degrees and are located at the same longitudinal position as each other along the elongate shaft 102. The catheters 300 and 400 can be in communication with or can include a propulsion system configured to, when the balloon wall is in contact with a vessel wall, propel a fluid from the first orifice toward the balloon wall to create an inertial impulse in a vessel wall to transfer momentum to a vascular lesion.

Figure 5:
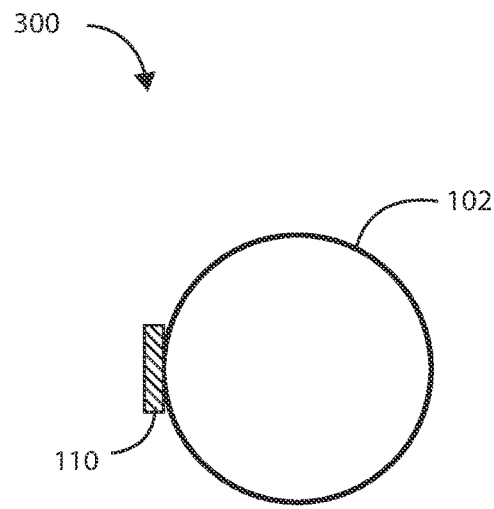
FIG. 5 is a schematic cross-sectional view of additional configurations the catheter system of FIG. 3 along line 5-5' in accordance with various embodiments herein.

The orifice or multiple orifices can assume many configurations about the elongate shaft of the catheters described herein. Examples of catheters having one or multiple orifices at different positions around the circumference of the catheter are shown in FIGS. 5-8. Referring now to FIG. 5, a schematic cross-sectional view of a portion of catheter 300 of FIG. 3 along line 5-5' in FIG. 3 is shown in accordance with various embodiments herein. Catheter 300 includes an elongate shaft 102 and a first orifice 110.

Figure 6:
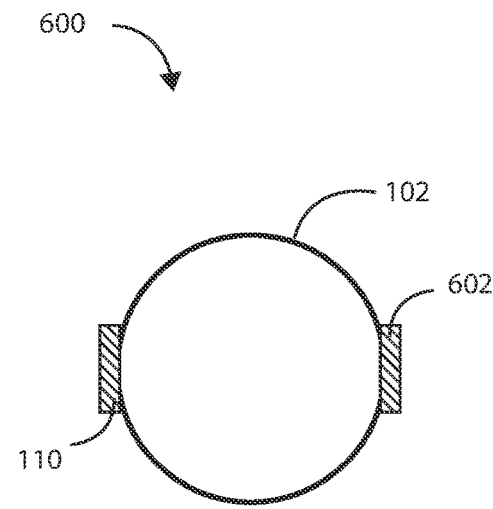
FIGS. 6-8 are schematic cross-sectional views of the catheter system of FIG. 5 along line 5-5' in accordance with various embodiments herein.
Figure 7:
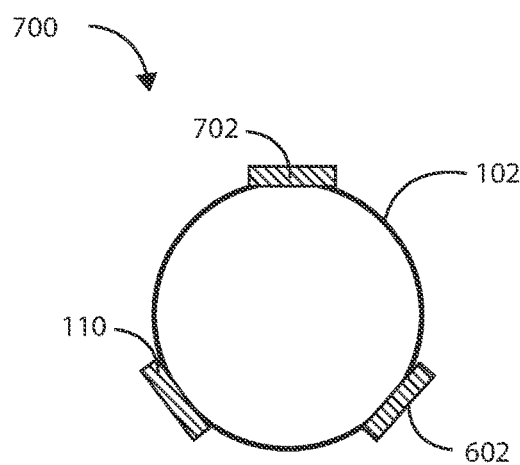
Figure 8:
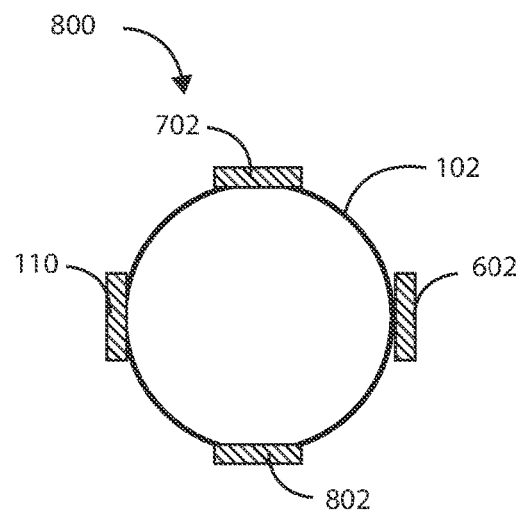

Referring now to FIGS. 6-8 schematic cross-sectional views of additional configurations for catheters having multiple orifices disposed circumferentially are shown in accordance with various embodiments herein. The configuration of catheter 600 in FIG. 6 includes an elongate shaft 102, a first orifice 110, and a second orifice 602, where the first orifice 110 and the second orifice 602 are separated by about 180 degrees around the circumference of elongate shaft 102. The configuration of catheter 700 in FIG. 7 includes an elongate shaft 102, a first orifice 110, a second orifice 602, and a third orifice 702, where the first orifice 110, the second orifice 602, and the third orifice 702 are separated from each other by about 120 degrees around the circumference of elongate shaft 102. The configuration of catheter 800 shown in FIG. 8 includes an elongate shaft 102, a first orifice 110, a second orifice 602, a third orifice 702, and a fourth orifice 802, where the first orifice 110, the second orifice 602, the third orifice 702, and the fourth orifice 802 are separated from each other by about 90 degrees around the circumference of elongate shaft 102.

Multiple orifices in various configurations can be suitable for use with the catheters herein. When multiple orifices are present, the orifices can be radially offset from one another by about 1 degree to about 360 degrees. In some embodiments, the orifices can be radially offset from one another by at least about or about 45 degrees. In some embodiments, the orifices can be radially offset from one another by at least about or about 60 degrees. In some embodiments, the orifices can be radially offset from one another by at least about or about 90 degrees. In some embodiments, the orifices can be radially offset from one another by at least about or about 180 degrees. In some embodiments, a plurality of orifices will be evenly spaced and radially offset from each other so that where there are n orifices, they are spaced apart by 360 degrees divided by n. In other embodiments, the orifices will be unevenly spaced and radially offset from each other.

The orifices along the elongate shafts herein can include many configurations. In some embodiments, the orifices along the elongate shaft are spaced around a diameter of the elongate shaft, are spaced along a length of the elongate shaft, or both. In some embodiments, the orifices along the elongate shaft are spaced equally around the diameter of the elongate shaft. In some embodiments, the orifices can form one or more circular patterns about the elongate shaft. In some embodiments, the orifices can be clustered in groups of two or more orifices about the elongate shaft. In some embodiments, the orifices can be aligned along parallel lines along the elongate shaft. In some embodiments, the orifices can form a spiral configuration about the longitudinal axis of the elongate shaft of the catheter. In some embodiments, the spiral configuration can run clockwise about the longitudinal axis of the elongate shaft of the catheter, while in other embodiments the spiral configuration can run counter-clockwise about the longitudinal axis of the elongate shaft of the catheter. In some embodiments, the orifices can form a single helix, a double helix, a triple helix, or a quadruple helix about the longitudinal axis of the elongate shaft of the catheter.

The orifices can assume many shapes, including, but not to be limited to circles, squares, rectangles, triangles, pentagons, hexagons, and the like. The size of the orifices herein can include those having a largest dimension of from 0.1 mm and 2 mm. In some embodiments, the largest dimension of the orifices suitable for use herein can be greater than or equal to 0.1 mm, 0.2 mm, 0.3 mm, 0.4 mm, 0.5 mm, 0.6 mm, 0.7 mm, 0.8 mm, 0.9 mm, or 1.0 mm, 1.1 mm, 1.2 mm, 1.3 mm, 1.4 mm, 1.5 mm, 1.6 mm, 1.7 mm, 1.8 mm, 1.9 mm, or 2.0 mm, or can be an amount falling within a range between any of the foregoing. In the case of circular orifices, the diameter of the circular orifices can include those having a diameter from 0.1 mm to 2 mm. The size of the orifices herein, including circular orifices, can include those having a diameter of from 0.1 mm and 2 mm. In some embodiments, the largest dimension of the orifices suitable for use herein can be greater than or equal to 0.1 mm, 0.2 mm, 0.3 mm, 0.4 mm, 0.5 mm, 0.6 mm, 0.7 mm, 0.8 mm, 0.9 mm, or 1.0 mm, 1.1 mm, 1.2 mm, 1.3 mm, 1.4 mm, 1.5 mm, 1.6 mm, 1.7 mm, 1.8 mm, 1.9 mm, or 2.0 mm, or can be an amount falling within a range between any of the foregoing.

It will be appreciated that the catheters herein can include any number of orifices that can generate a corresponding number of fluid jets. For example, in some embodiments, the catheters herein can include from one orifice to ten orifices. In other embodiments, the catheters herein can include from five to fifteen orifices. In yet other embodiments, catheters herein can include from ten orifices to thirty orifices. The catheters herein can include one, two, three, four, five, six, seven, eight, nine, or ten orifices. The catheter systems can include 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 orifices. It will be appreciated that catheters herein can include any number of orifices that can fall within a range, where any of the forgoing numbers can serve as the lower or upper bound of the range, provided that the lower bound of the range is a value less than the upper bound of the range. In some embodiments, the catheter systems herein can include more than 40 orifices.

It will be appreciated that the orifices herein are suitable for propelling a fluid jet toward a balloon wall at a minimum velocity of 1 meters per second (m/s), 5 m/s, or 10 m/s, where the velocity is measured where a fluid jet exits from an orifice. In some embodiments, the velocity of the fluid jet being propelled from each orifice can be greater than or equal to 1 m/s, 5 m/s, 10 m/s, 20 m/s, 30 m/s, 40 m/s, 50 m/s, 60 m/s, 70 m/s, 80 m/s, 90 m/s, 100 m/s, 110 m/s, 120 m/s, 130 m/s, 140 m/s, 150 m/s, 160 m/s, 170 m/s, 180 m/s, 190 m/s, 200 m/s, 210 m/s, 220 m/s, 230 m/s, 240 m/s, or 250 m/s, or can be an amount falling within a range between any of the foregoing.

Figure 9:
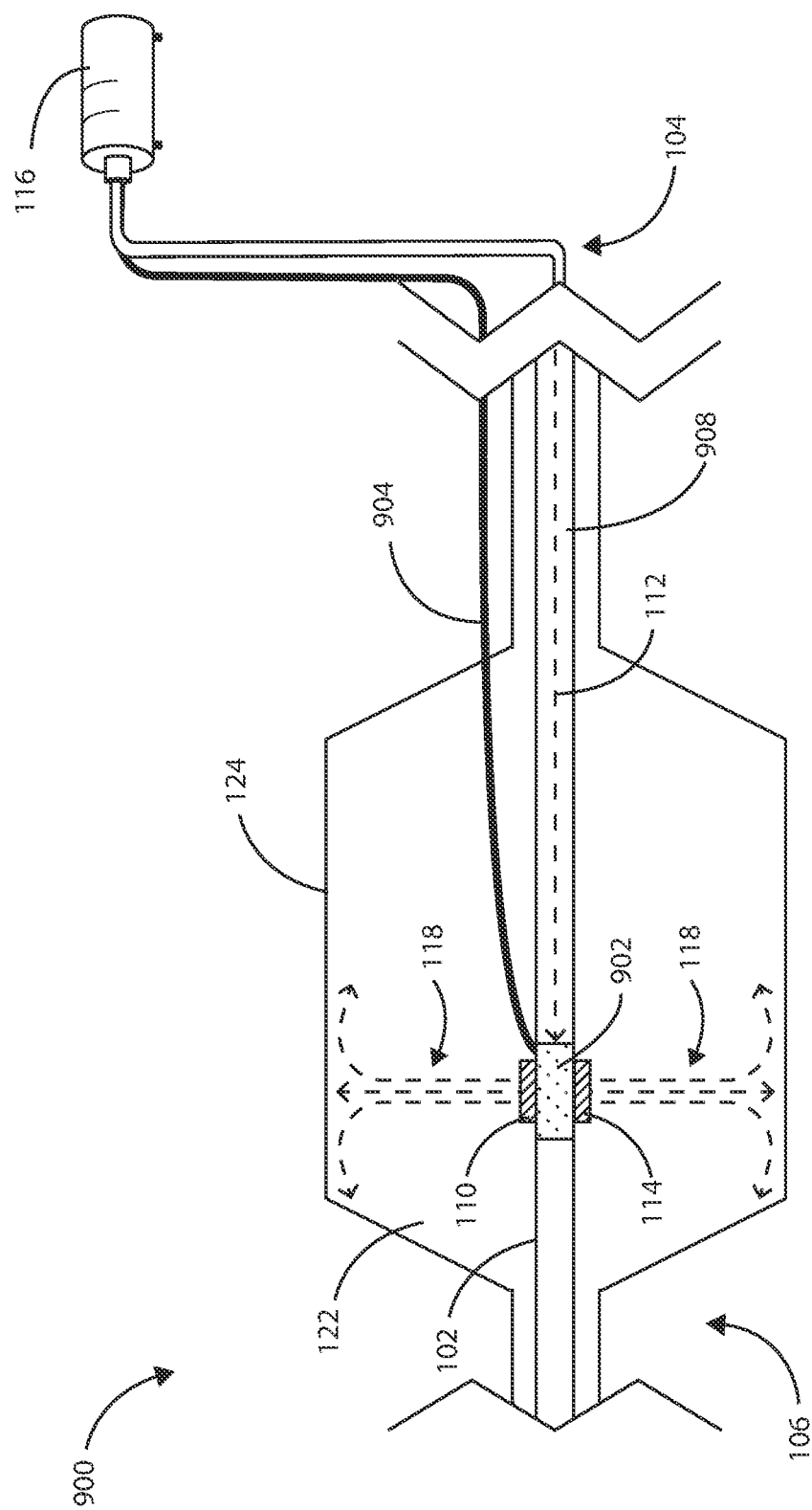
FIG. 9 is a schematic cross-sectional view of a catheter system in accordance with various embodiments herein.
Figure 10:
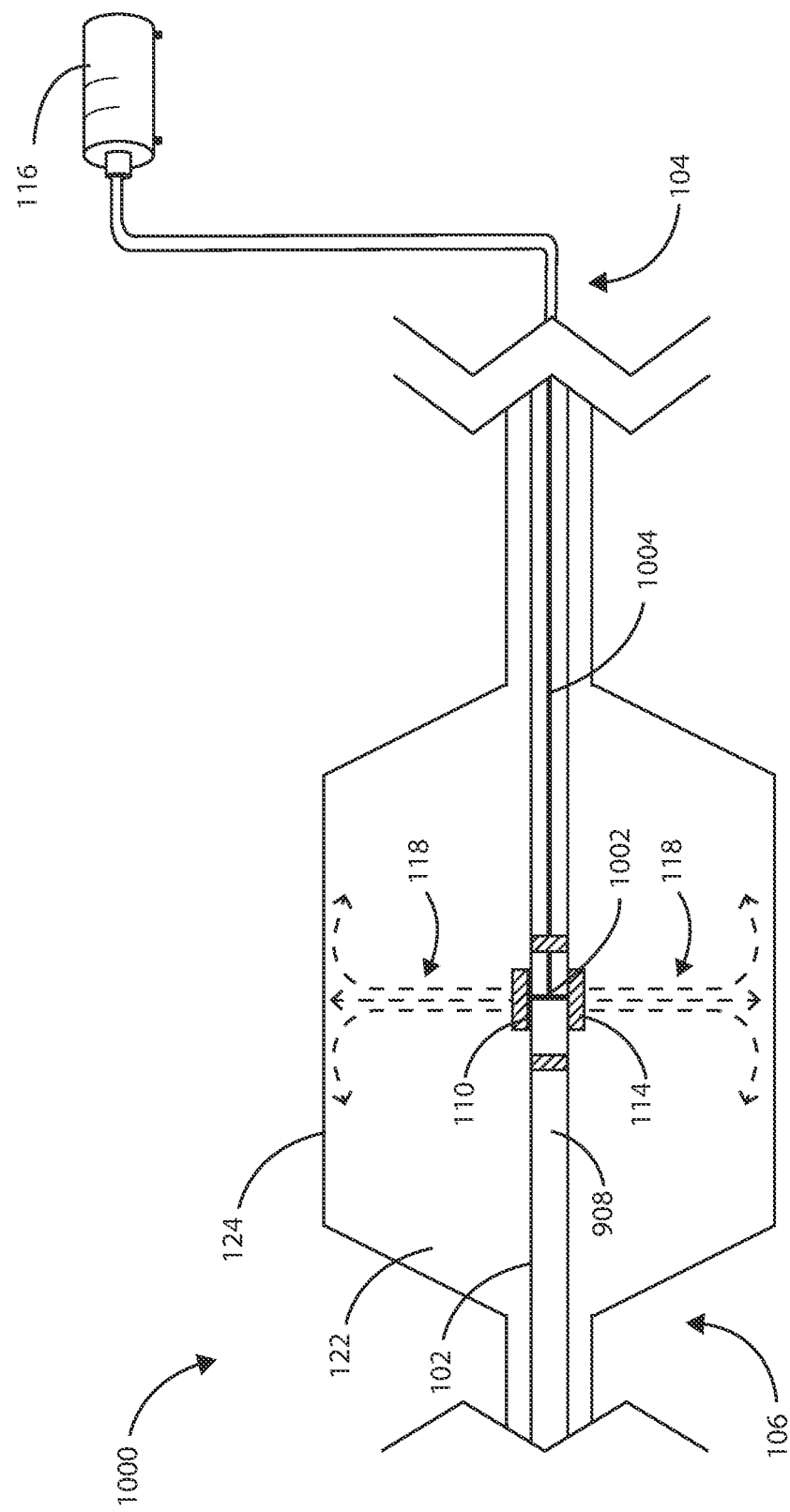
FIG. 10 is a schematic cross-sectional view of a catheter system in accordance with various embodiments herein.

External High Pressure Fluid Source with Internal Actuator Embodiments (FIGS. 9-10)

The catheter systems herein can include one or more actuation valves for directing a fluid through the orifices of the catheters to create one or more fluid jets propelled from each orifice. In some embodiments, the one or more fluid jets are pulsed fluid jets. The catheter system can have an external fluid source that is pulsed using mechanisms outside of the body as described with respect to FIG. 1, and as also possible in the embodiments of FIGS. 3 and 4, or can be pulsed using a mechanism located at the distal end of the catheter, such as an actuator. Referring now to FIG. 9, a schematic cross-sectional view of a catheter 900 is shown in accordance with various embodiments herein where an electromechanical valve or actuator is provided at the distal portion of the catheter to provide the pulsing of the fluid jet. Catheter 900 includes an elongate shaft 102 extending from a proximal region 104 to a distal region 106. The elongate shaft 102 can define a propulsion fluid lumen 908 and at least a first orifice 110 for fluid flow 112 through the first orifice 110. In some embodiments, catheter 900 includes an elongate shaft 102, where the elongate shaft 102 defines at least a first orifice 110 and a second orifice 114 for fluid flow, and where the first orifice 110 and second orifice 114 are spaced from each other circumferentially. The catheter 900 can include a balloon 122 coupled to the elongate shaft 102 and surrounding the first orifice 110, and if present, the second orifice 114. The balloon 122 can include a balloon wall 124 and be configured to expand from a collapsed configuration suitable for advancing the catheter through a patient's vasculature to a first expanded configuration suitable for anchoring the catheter in position relative to a treatment site.

The catheter 900 can be in fluid communication with a propulsion system including an external fluid flow source 116 in fluid communication with a proximal region 104 of the propulsion fluid lumen 908 and an actuation valve 902 at a distal region 106 of the propulsion fluid lumen 908. The external fluid flow source 116 can provide a high-pressure fluid flow. The fluid propulsion system can be configured to create a pulsed fluid jet 118 propelled from the first orifice 110, and if present, from the second orifice 114. In some embodiments, the catheter 900 can include a second orifice 114 through which the actuation valve 902 can create a pulsed fluid jet 118 propelled from the second orifice 114. When the balloon wall of catheter 900 is in contact with a vessel wall, the propulsion system can be used to propel a fluid from the first orifice toward the balloon wall to create an inertial impulse in a vessel wall to transfer momentum to a vascular lesion. While not depicted in FIG. 9, it will be appreciated that in some embodiments, the actuation valve 902 is located at a proximal region 104 of the catheter 900.

Actuation of the actuation valve 902 can create a pulsed fluid jet 118 through any number of orifices disposed along the elongate shaft 102 and can direct the pulsed fluid jet 118 toward the surface of the balloon wall 124. The actuation valve 902 can be tuned to a given dwell time to open and close the orifice(s) to create discrete pulses of fluid from the orifice(s) at a rate of from 1 Hertz (Hz) to 300 Hz. Actuation valve 902 can be in electrical communication with a control wire 904 extending along or through the elongate shaft 102 that is in further electrical communication with a controller that can be co-located with external fluid flow source 116. In some embodiments, the controller can be a stand-alone unit. The actuation valve 902 can include, but is not to be limited to, an electromechanical valve, such as a servomotor, or an electromagnetic plunger.

The timing of activation of the fluid jets can be controlled to create various therapeutic fatigue modes for disrupting a vascular lesion. The fluid jets can be timed to be activated from 1 Hz to 300 Hz. In some embodiments, the fluid jets can be timed to be activated from 10 Hz to 100 Hz. In some embodiments, the fluid jets can be timed to be activated from 100 Hz to 300 Hz. In some embodiments, the frequency can be greater than or equal to 1 Hz, 2 Hz, 3 Hz, 4 Hz, 5 Hz, 6 Hz, 7 Hz, 8 Hz, 9 Hz, or 10 Hz, 20 Hz, 30 Hz, 40 Hz, 50 Hz, 60 Hz, 70 Hz, 80 Hz, 90 Hz, or 100 Hz, 120 Hz, 140 Hz, 160 Hz, 180 Hz, 200 Hz, 220 Hz, 240 Hz, 260 Hz, 280 Hz, or 300 Hz or can be an amount falling within a range between any of the foregoing.

In some embodiments, the timing of the fluid jets from the orifices can be tailored to be activated synchronously or asynchronously depending on the therapeutic fatigue mode desired. In some embodiments, a first series of orifices aligned along a first longitudinal axis can be activated at time zero, followed by a second series of orifices aligned along a second longitudinal axis at time x, where the first series of orifices are disposed about the short axis of the catheter at a distance that is 180 degrees apart from the second series of orifices and where time x can be any time within the nanosecond, microsecond, or millisecond time scales. The first and second series of orifices can be activated for multiple cycles. It will be appreciated that multiple series of orifices can be contemplated herein, including a third series of orifices, a fourth series of orifices, a fifth series of orifices, and so on. There are many options for orifice configurations as described herein. Any of the many orifice configurations described herein can be used with the propulsion system embodiment of FIG. 9.

An additional embodiment for the actuation valves herein can include a rotary mechanical valve. Referring now to FIG. 10, a schematic cross-sectional view of a catheter 1000 is shown in accordance with various embodiments herein. Catheter 1000 includes an elongate shaft 102 extending from a proximal region 104 to a distal region 106. The elongate shaft 102 can define a propulsion fluid lumen 908 and at least a first orifice 110 for fluid flow through the first orifice 110. In some embodiments, the catheter 1000 can include a second orifice 114 through which the rotary mechanical valve 1002 can create a pulsed fluid jet 118 propelled from the second orifice 114.

The catheter 1000 can be in fluid communication with a propulsion system including an external fluid flow source 116 in fluid communication with a distal region 106 of the propulsion fluid lumen 908 and a rotary mechanical valve 1002 at a distal region 106 of the propulsion fluid lumen 908 configured to create a pulsed fluid jet 118 propelled from the first orifice 110. The external fluid flow source 116 can provide a high-pressure source of fluid. When the balloon wall of catheter 1000 is in contact with a vessel wall, the propulsion system can be used to propel a fluid from the first orifice toward the balloon wall to create an inertial impulse in a vessel wall to transfer momentum to a vascular lesion.

The rotary mechanical valve 1002 within the propulsion fluid lumen 908 of catheter 1000 can be in communication with a rotary control shaft 1004 extending along or through the elongate shaft 102. In some embodiments, the catheter 1000 can include a second orifice 114 through which the rotary mechanical valve 1002 can create a pulsed fluid jet 118 propelled from the second orifice 114. The rotary mechanical valve 1002 can rotate within the propulsion fluid lumen 908 at an angular velocity suitable to open and close the orifice(s) to create discrete pulses of fluid from the orifice(s). The pulses of fluid have at a minimum a velocity of 1 meters per second (m/s), 5 m/s, or 10 m/s, where the velocity of the fluid is measured where a fluid jet exits from the first orifice.

Figure 11:
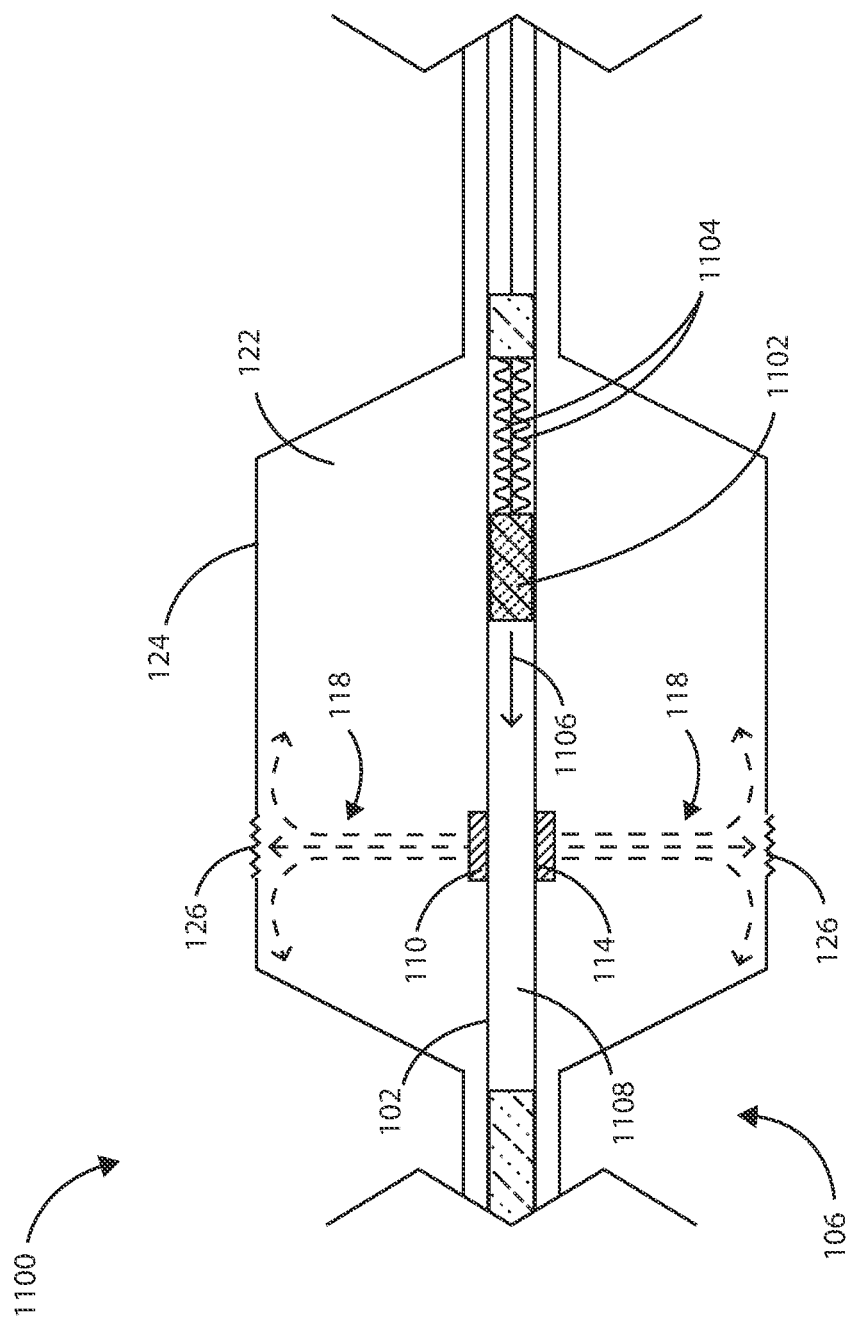
FIG. 11 is a schematic cross-sectional view of a catheter system in accordance with various embodiments herein.
Figure 12:
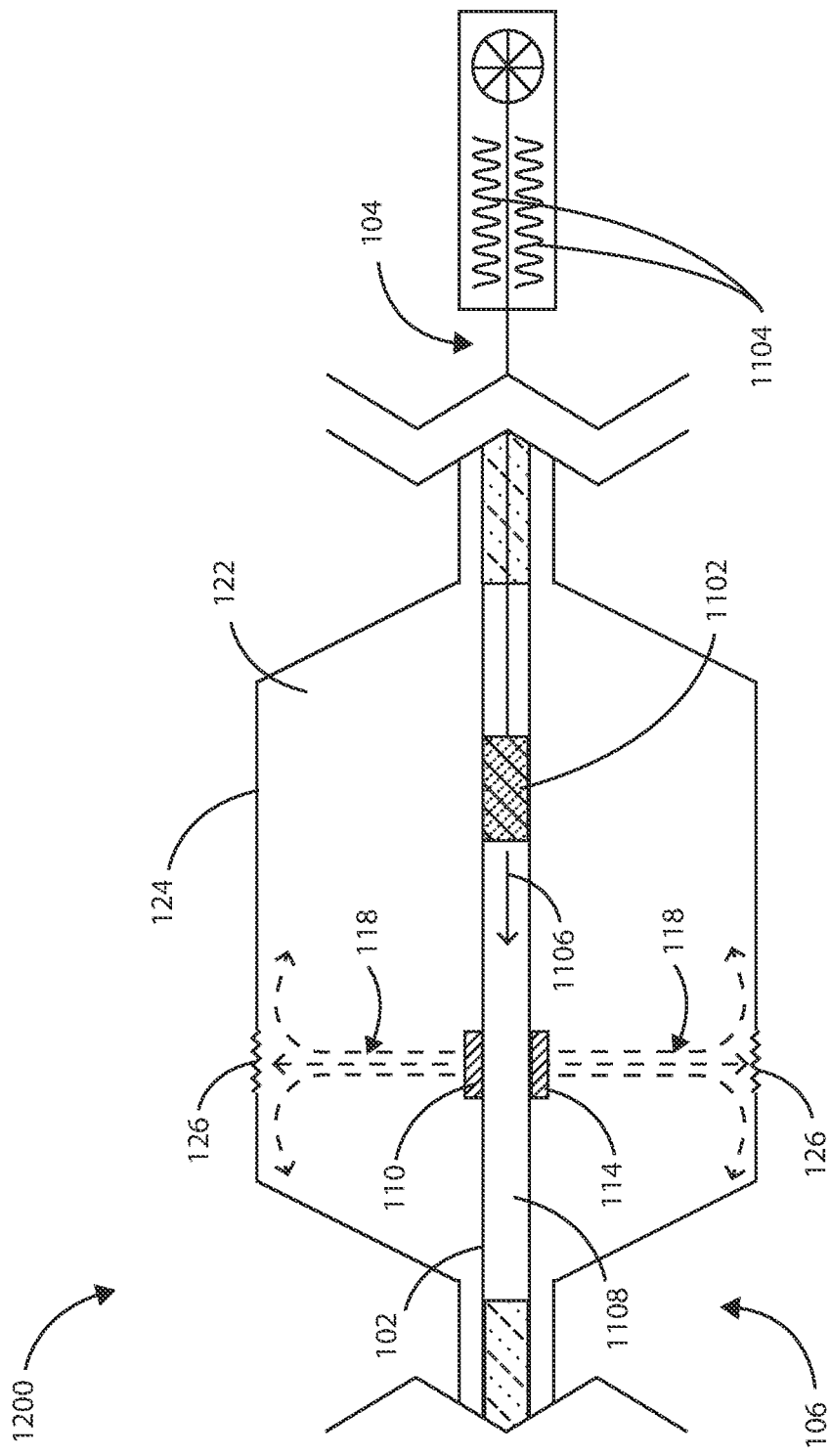
FIG. 12 is a schematic cross-sectional view of a catheter system in accordance with various embodiments herein.
Figure 13:
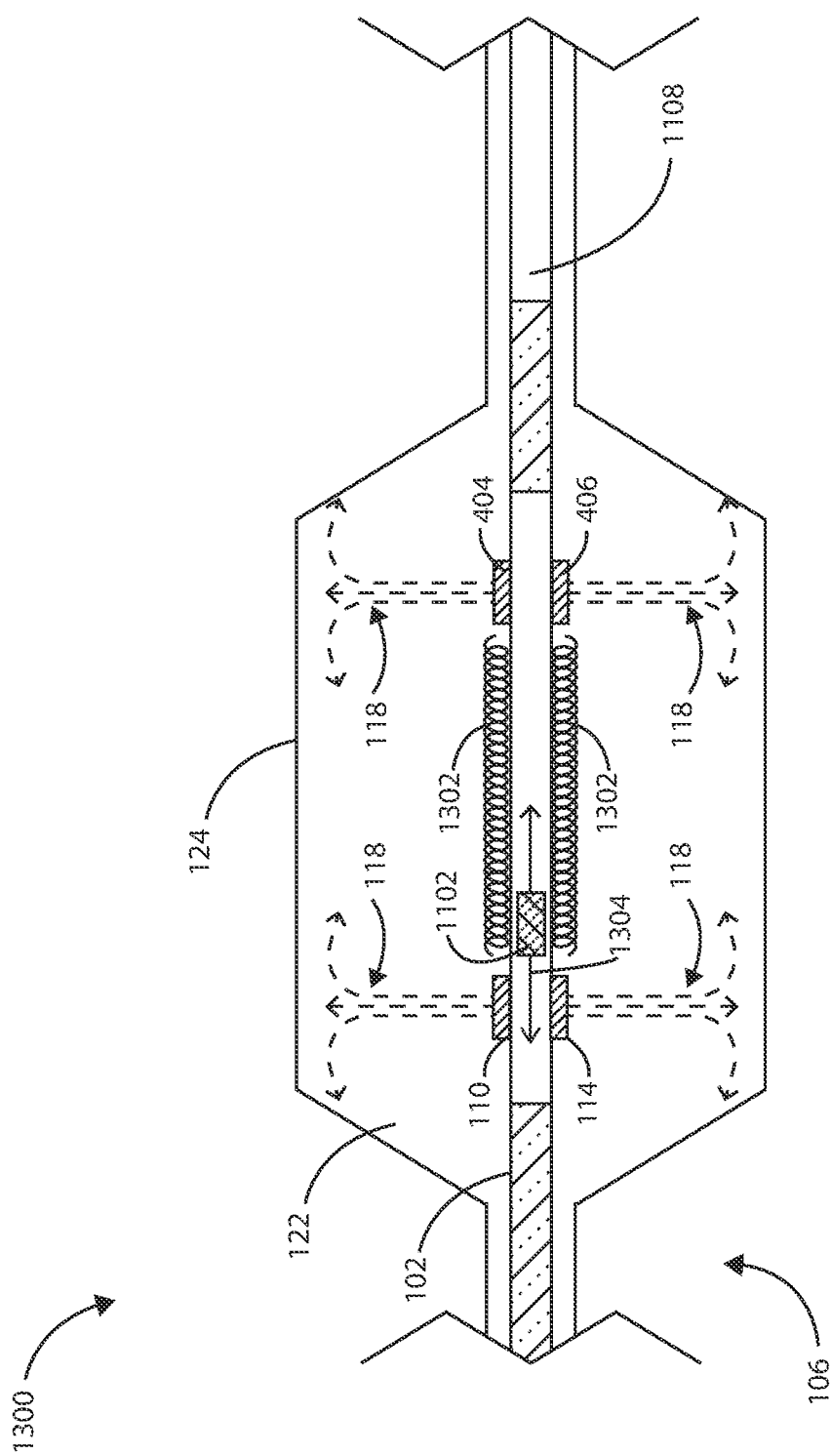
FIG. 13 is a schematic cross-sectional view of a catheter system in accordance with various embodiments herein.

Piston Embodiments (FIGS. 11-13)

The catheter systems herein can include propulsion systems having one or more piston mechanisms for directing a fluid through the orifices of the catheters to create one or more fluid jets propelled from each orifice. A mechanical system can be used to propel the piston, which in turn accelerates fluid within a piston lumen out of an orifice, directing the high velocity fluid toward the balloon wall. In these systems, an external fluid supply is included to inflate the balloon with balloon fluid. The external fluid supply does not need to be a high-pressure fluid source because the piston and piston-moving mechanical system at a distal end of the catheter propels the fluid.

Referring now to FIGS. 11-13, schematic cross-sectional views of catheters 1100, 1200, and 1300 are shown in accordance with various embodiments herein. FIG. 11 shows a distal region of a configuration where a catheter 1100 includes balloon 122 having a balloon wall 124. The catheter can include an elongate shaft 102 extending from a proximal region to a distal region 106 and can also include a piston lumen 1108. The propulsion system can include a piston 1102 located within piston lumen 1108, such as a mechanical spring piston. The piston lumen 1108 can be defined by the elongate shaft 102 at a distal region 106 of the elongate shaft 102. The elongate shaft 102 can include a first orifice 110 and a second orifice 114 for fluid flow through each orifice. The piston 1102 can be in contact with a mechanical spring 1104 located at a distal region 106 of the elongate shaft 102 and configured to accelerate the piston 1102 in the direction of arrow 1106 to propel fluid as fluid jet 118 from the first orifice 110 and the second orifice 114 such that fluid jet 118 exits from each orifice toward the balloon wall 124 and creates an inertial impulse 126 at the balloon wall 124. When the balloon wall of catheter 1100 is in contact with a vessel wall, the propulsion system can be used to propel a fluid from the first orifice toward the balloon wall to create an inertial impulse in a vessel wall to transfer momentum to a vascular lesion. In the configuration shown in FIG. 12, catheter 1200 includes a piston 1102 at a distal region 106 and a mechanical spring 1104 at a proximal region 104. The catheter 1200 includes balloon 122 having a balloon wall 124. The catheter can also include a piston lumen 1108. The propulsion system can include the piston 1102 located within piston lumen 1108. The piston lumen 1108 can be defined by the elongate shaft 102 at a distal region 106 of the elongate shaft 102. The elongate shaft 102 can include a first orifice 110 and a second orifice 114 for fluid flow through each orifice. The piston 1102 can be in mechanical communication with the mechanical spring 1104 located at the proximal region 104 of the elongate shaft 102, such as by a shaft element running along the elongate shaft 102. The mechanical spring 1104 can be outside of the patient's body. The mechanical spring 1104 and shaft element can be configured to accelerate the piston 1102 in the direction of arrow 1106 to propel fluid as fluid jet 118 from the first orifice 110 and the second orifice 114 such that fluid jet 118 exits from each orifice toward the balloon wall 124 and creates an inertial impulse 126 at the balloon wall 124. When the balloon wall of catheter 1200 is in contact with a vessel wall, the propulsion system can be used to propel a fluid from the first orifice toward the balloon wall to create an inertial impulse in a vessel wall to transfer momentum to a vascular lesion.

Without being bound by any particular theory, it is believed that mechanical springs in contact with the pistons herein are governed by Hooke's law. Hooke's law provides that the force required for the extension or compression of a spring, including a spring with a piston at its free end, is directly proportional to the distance of extension or compression. Hooke's law is expressed mathematically as $F=-kx$, where F is the force applied to a spring in Newtons per meter (N/m), k is the spring constant for a given spring and is a measure of the spring's stiffness, and x is the distance in meters (m) that the free end of the spring is displaced from a relaxed equilibrium position.

In FIGS. 11 and 12, when the balloon is filled with balloon fluid to inflate the balloon, the balloon fluid may fill the piston lumen 1108 with balloon fluid. Alternatively, or in addition, when the mechanical spring 1104 is moved from a released position to a cocked position, drawing back the piston, that motion may draw fluid into the piston lumen 1108. The propulsion system includes a cocking mechanism configured to draw the spring and piston from released position to a cocked position. The cocking mechanism can include a linear control element extending along or through the elongate lumen and a trigger accessible to a caregiver. Alternatively, the piston 1102 and mechanical spring 1104 may be in the cocked position when the catheter is introduced to the body.

In the configuration shown in FIG. 13, an electromagnetic system is used to drive the motion of a piston within a piston lumen. FIG. 13 shows the distal region of catheter 1300 which includes a balloon 122 having a balloon wall 124. The catheter can include an elongate shaft 102 extending from a proximal region to a distal region 106 and can also include a piston lumen 1108.

The propulsion system can include a piston 1102 located within piston lumen 1108. The piston lumen 1108 can be defined by the elongate shaft 102 at a distal region 106 of the elongate shaft 102. The elongate shaft 102 can include a first orifice 110 and a second orifice 114 for fluid flow through each orifice. The elongate shaft 102 can further include a third orifice 404 and a fourth orifice 406 for fluid flow through each orifice. When the balloon wall of catheter 1300 is in contact with a vessel wall, the propulsion system can be used to propel a fluid from the first orifice toward the balloon wall to create an inertial impulse in a vessel wall to transfer momentum to a vascular lesion.

The propulsion system of catheter 1300 can include an electromagnet 1302 surrounding the piston lumen 1108, where the electromagnet 1302 is configured to be energized to accelerate the piston 1102 along the piston lumen 1108. Accelerating the piston 1102 in the distal direction causes a fluid jet 118 to be propelled from each of the first orifice 110 and the second orifice 114. Accelerating the piston 1102 in the proximal direction causes a fluid jet 118 to be propelled from each of the third orifice 404 and the fourth orifice 406. It will be appreciated that while four orifices are shown in catheter 1300, many different number and configuration of orifices can be used as discussed herein. The electromagnet 1302 can be configured to be energized to accelerate the piston 1102 back and forth between a proximal region of the piston lumen 1108 and a distal region of the piston lumen 1108 as indicated by arrow 1304. In some embodiments, cycling the piston 1102 back and forth within the piston lumen 1108 can produce multiple fluid jets 118 from each orifice along the elongate shaft 102. In some embodiments, the elongate shaft 102 of catheter 1300 defines the first orifice 110 and a second orifice 114 at a distal region of the piston lumen 1108 within the balloon 122 and further defines a third orifice 404 and a fourth orifice 406 at a proximal region of the piston lumen 1108 within the balloon 122. Materials suitable for the piston in the embodiment in catheter 1300 include electromagnetic materials.

In the embodiment of FIG. 13, when the balloon is filled with balloon fluid to inflate the balloon, the balloon fluid may fill the piston lumen 1108 with balloon fluid via one of the orifices. Alternatively, or in addition, when the electromagnet 1302 is activated to move the piston, that motion may draw fluid into the piston lumen 1108 via one or more of the orifices. The propulsion system may include a control wire (not shown in FIG. 13) in electrical communication with both the electromagnet and with a controller outside of the body. The control wire can extend along or through the elongate shaft 102. The controller can be co-located with an external fluid flow source used to inflate the balloon with balloon fluid. In some embodiments, the controller can be a stand-alone unit.

Figure 14:
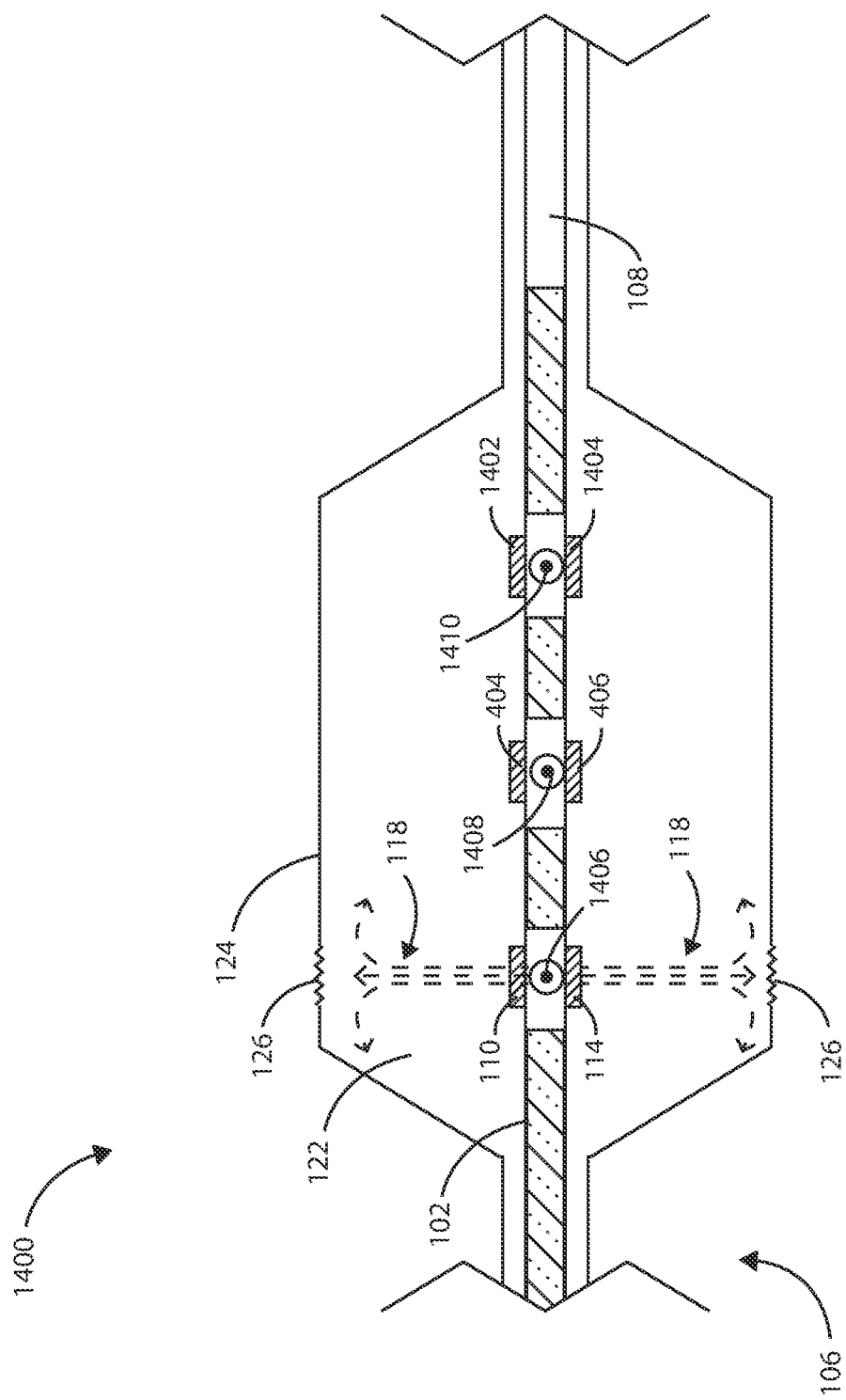
FIG. 14 is a schematic cross-sectional view of a catheter system in accordance with various embodiments herein.

Explosive Charge Embodiments (FIG. 14)

The propulsion systems herein can further include multiple explosive charges distributed along the length of the elongate shafts of the catheters described. Referring now to FIG. 14, a schematic cross-sectional view of a distal region of a catheter 1400 is shown in accordance with various embodiments herein. Catheter 1400 includes balloon 122 having a balloon wall 124. The catheter 1400 can include an elongate shaft 102 extending from a proximal region to a distal region 106 and can also include a lumen 108. The lumen 108 can be defined by the elongate shaft 102 at a distal region 106 of the elongate shaft 102. The catheter 1400 can include one or more explosive charges located within the lumen 108 of elongate shaft 102. The elongate shaft 102 can include a first orifice 110 and a second orifice 114, where the first orifice 110 and the second orifice 114 are disposed adjacent to a first explosive charge 1406 such that, when detonated, a fluid within the lumen 108 of the elongate shaft 102 is rapidly accelerated as a fluid jet 118 within the balloon 122 toward the balloon wall 124 to generate an inertial impulse 126 in a vessel wall to transfer momentum to a vascular lesion.

The catheter 1400 can include additional explosive charges and orifices along the length of the elongate shaft 102. The catheter 1400 can include a third orifice 404 and a fourth orifice 406, where the third orifice 404 and a fourth orifice 406 are disposed adjacent to the second explosive charge 1408. The catheter 1400 can further include a fifth orifice 1402 and a sixth orifice 1404, where the fifth orifice 1402 and the sixth orifice 1404 are disposed adjacent to a second explosive charge 1410.

In one embodiment, the explosive charges are single-use, high-energy density charges. One example of a material that can be used as an explosive charge is lead azide explosive material, such as 5 milligrams of lead azide explosive material. The explosive charge can be provided within an explosive chamber, such as a cylindrical explosive chamber. In one example, the cylindrical explosive chamber is made of stainless steel. In one example, the explosive chamber includes an orifice of the chamber that is closed with epoxy resin to provide protection from fluid until detonation.

The explosive charges herein can be configured to detonate all at once or can be configured to detonate one at a time. In some embodiments, the explosive charges can be configured to detonate in series, with a predetermined time lag between detonations. In some embodiments, the catheter 1400 can include from 2 to 30 explosive charges. In some embodiments, the 1400 can include from 30 to 100 explosive charges. In some embodiments, the number explosive charges along the catheter 1400 can be greater than or equal to 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, or 100 charges, or can be an amount falling within a range between any of the foregoing.

The explosive charges may be detonated with an electrical current and the propulsion system may include a control wire in electrical communication with the one or more explosive charges and with a controller outside of the body. The control wire or wires (not shown in FIG. 14) can extend along or through the elongate shaft 102. The controller can be co-located with an external fluid flow source used to inflate the balloon with balloon fluid. In some embodiments, the controller can be a stand-alone unit.

Methods

Figure 15:
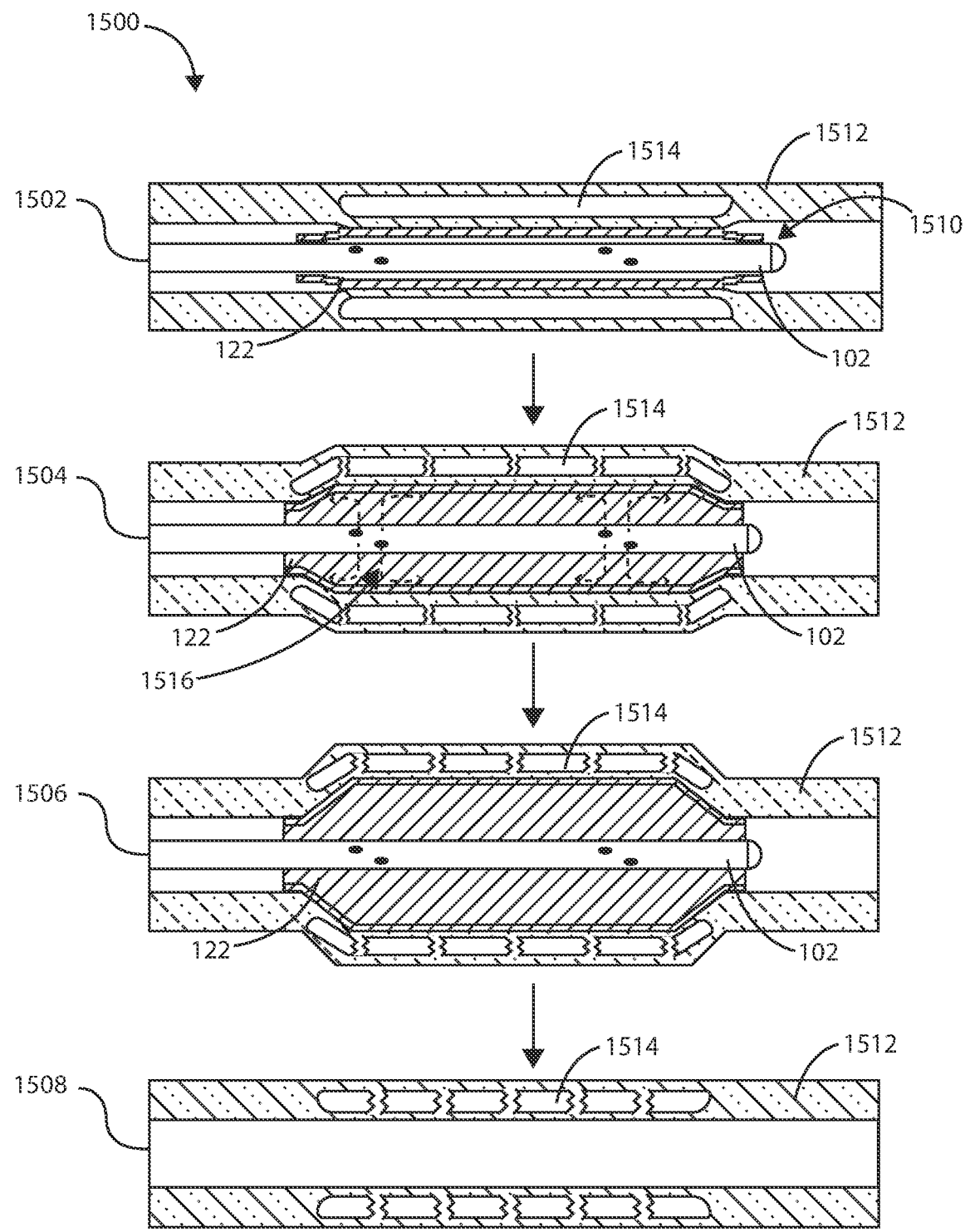
FIG. 15 is a schematic flow diagram for a method in accordance with the various embodiments herein.

The catheter systems described herein can be used in one or more methods for generating pressure to induce fractures upon a vascular lesion within or adjacent a vessel wall of a blood vessel as described herein. Referring now to FIG. 15, a schematic flow diagram for a method 1500 is shown in accordance with the various embodiments herein. Method 1500 includes advancing a catheter 1510 to a treatment site 1514 within the blood vessel 1512, the catheter 1510 including an elongate shaft 102 and a balloon 122 coupled to the elongate shaft 102 at 1502. The treatment site 1514 can include a vascular lesion within a patient's vasculature. In some embodiments, the vascular lesion can include a calcified lesion.

The method 1500 includes expanding the balloon 122 from a collapsed configuration suitable for advancing the catheter through a patient's vasculature to a first expanded configuration suitable for anchoring the catheter in position relative to the treatment site 1514 at 1504. After expanding the balloon 122 to a first expanded configuration, the method 1500 further includes propelling a fluid 1516 from a first orifice defined in the elongate shaft toward a balloon wall, thereby imparting pressure upon the treatment site 1514 lesion to induce fractures in the treatment site 1514. The method 1500 can also include, after propelling the fluid 1516, further expanding the balloon 122 from the first expanded configuration to a second further expanded configuration at 1506. The method can include collapsing the balloon back to the collapsed configuration and completely removing the catheter 1510 from the patient's vasculature at 1508.

Propelling fluids in the methods herein can include propelling a fluid toward the balloon wall at a minimum velocity of 1 meters per second (m/s), 5 m/s, or 10 m/s, where the velocity is measured where a fluid jet exits from the first orifice. Additional velocities suitable for propelling fluids are described elsewhere herein. Propelling fluids in the methods herein can include operating an actuation valve located at a proximal region of a propulsion fluid lumen outside of the patient's body or operating an actuation valve at a distal region of a propulsion fluid lumen defined in the elongate shaft to pulse the fluid from an external high-pressure fluid source and create a pulsed jet of fluid. The actuation valve can include an electromechanical actuation valve or a mechanical rotary valve. Activating the actuation valve can include applying a voltage to a control wire extending along the elongate shaft. Propelling fluids may also include activating a piston-spring system where the spring is at the distal end of the elongate shaft, activating a piston-spring system where the spring is at the proximal end of the elongate shaft, activating an electromechanical piston system, or detonating an explosive charge.

Balloons

The balloons suitable for use in the catheter systems herein include those that can be passed through the vasculature of a patient when in a collapsed configuration. In some embodiments, the balloons herein are made from silicone. In other embodiments, the balloons herein are made from polydimethylsiloxane (PDMS), polyurethane, polymers such as PEBAX™ material available from Arkema, which has a location at King of Prussia, Pennsylvania, USA, nylon, and the like. In some embodiments, the balloons can include those having diameters ranging from 1 millimeter (mm) to 25 mm in diameter. In some embodiments, the balloons can include those having diameters ranging from 1.5 mm to 12 mm in diameter. In some embodiments, the balloons can include those having diameters ranging from 1 mm to 5 mm in diameter. In some embodiments, the diameter can be greater than or equal to 0.5 mm, 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, 10.5 mm, 11.0 mm, 11.5 mm, 12.0 mm, 12.5 mm, 13.0 mm, 13.5 mm, 14.0 mm, 14.5 mm, 15.0 mm, 15.5 mm, 16.0 mm, 16.5 mm, 17.0 mm, 17.5 mm, 18.0 mm, 18.5 mm, 19.0 mm, 19.5 mm, or 20.0 mm, or can be an amount falling within a range between any of the foregoing.

In some embodiments, the balloons herein can include those having a length ranging from 5 mm to 300 mm in length. In some embodiments, the balloons herein can include those having a length ranging from 8 mm to 200 mm in length. In some embodiments, the length of the balloon can be greater than or equal to 5 mm, 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, 210 mm, 220 mm, 230 mm, 240 mm, 250 mm, 260 mm, 270 mm, 280 mm, 290 mm, or 300 mm, or can be an amount falling within a range between any of the foregoing.

The balloons herein can be inflated to inflation pressures from 1 atmosphere (atm) to 70 atm. In some embodiments, the balloons herein can be inflated to inflation pressures of from 6 atm to 20 atm. In some embodiments, the balloons herein can be inflated to inflation pressures of from 20 atm to 70 atm. In some embodiments, the balloons herein can be inflated to inflation pressures that can be greater than or equal to 1 atm, 10 atm, 20 atm, 30 atm, 40 atm, 50 atm, 60 atm, or 70 atm, or can be an amount falling within a range between any of the foregoing.

The balloons herein can include those having various shapes, including, but not to be limited to, a conical shape, a square shape, a rectangular shape, a spherical shape, a conical/square shape, a conical/spherical shape, an extended spherical shape, an oval shape, a tapered, shape, a bone shape, a stepped diameter shape, an offset shape, or a conical offset shape. In some embodiments, the balloons herein can include a drug eluting coating or a drug eluting stent structure. The drug elution coating or drug eluting stent structure can include one or more therapeutic agents including anti-inflammatory agents, anti-neoplastic agents, anti-angiogenic agents, and the like. Exemplary agents can include, but is not to be limited to paclitaxel, docetaxel, everolimus, and sirolimus, and analogs thereof.

Balloon Fluids

Exemplary balloon fluids suitable for use herein can include but are not to be limited to one or more of water, saline, contrast agent, fluorocarbons, perfluorocarbons, gases, such as carbon dioxide, and the like. In some embodiments, the balloon inflation fluids include a mixture of saline to contrast agent in a volume ratio of 50:50. In some embodiments, the balloon fluids include a mixture of saline to contrast agent in a volume ratio of 25:75. In some embodiments, the balloon fluids include a mixture of saline to contrast agent in a volume ratio of 75:25. The balloon fluids suitable for use herein can be tailored on the basis of composition, viscosity, and the like in order to manipulate the properties of the fluid jet. The balloon fluids suitable for use herein are biocompatible.

In some embodiments, the contrast agents used herein can include, but are not limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12).

Control Wire

In some embodiments, control wires convey energy from a generator outside of a patient's body to one or more propulsion system elements inside the catheter inside of a patient's body. The control wires are configured to electrically connect these elements to an external generator, battery, or other power source. The control wires can be situated in a number of different configurations, based on the particular implementation of the catheter. For example, a coaxial lead can be provided with an inner conductor and an outer conductor. A conductive element positioned within a lumen, on an inner surface, or on an outer surface of the elongate shaft can be used as a control wire. In alternative examples, a control wire can be a conductive trace within a lumen, on an inner surface, or on an outer surface of the elongate shaft. One example of a conductor that can be used is stainless steel. Another is copper.

Elongate Shaft Configurations

The elongate shafts herein can include one or more lumens that span the length of the elongate shaft. Referring now to FIGS. 16-21, schematic cross-sectional views of various embodiments of an elongate shaft having multiple lumens are shown in accordance with various embodiments herein. In some embodiments, the elongate shaft can define a guidewire lumen. In some embodiments, the elongate shaft defines an inflation lumen surrounding the guidewire lumen, where the inflation lumen is in fluid communication with a balloon at a distal portion of the elongate shaft. In other embodiments, the elongate shaft defines an inflation lumen disposed alongside the guidewire lumen, where the inflation lumen is in fluid communication with a balloon at a distal portion of the elongate shaft. The inflation lumen can also be used as a deflation lumen. In yet other embodiments, the elongate shaft defines at least one control lumen. The control lumen can contain a control wire, mechanical element, mechanical shaft, or other control mechanism, for example.

Figure 16:
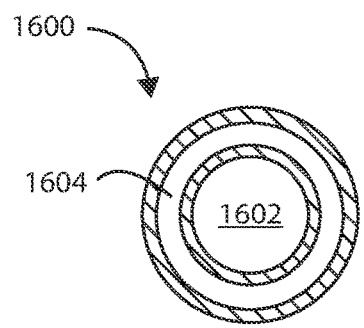
FIGS. 16-21 are schematic axial cross-sectional views of additional embodiments of an elongate shaft of a catheter in accordance with various embodiments herein.
Figure 17:
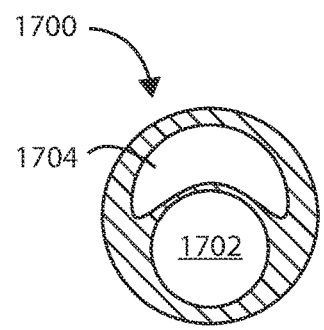
Figure 18:
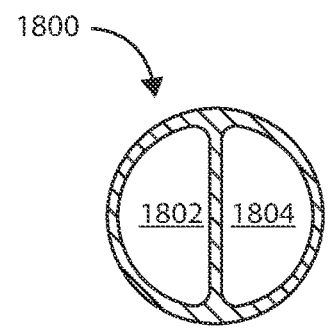
Figure 19:
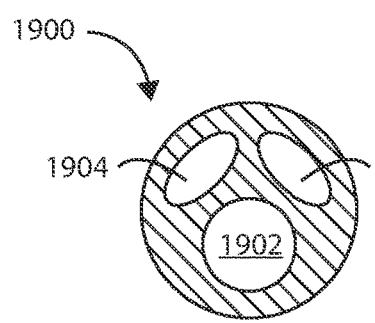
Figure 20:
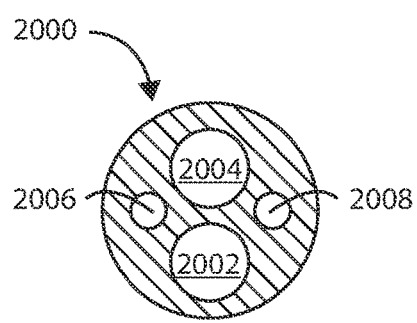
Figure 21:
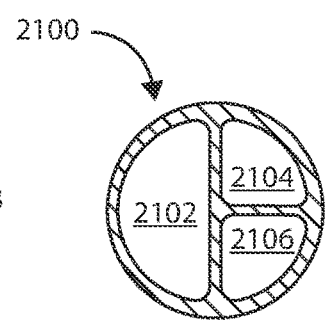

In the configuration in FIG. 16, elongate shaft 1600 includes concentrically disposed guidewire lumen 1602 and an inflation lumen 1604. In the configuration in FIG. 17, elongate shaft 1700 includes guidewire lumen 1702 and an inflation lumen 1704 disposed adjacent to and partially surrounding guidewire lumen 1702. In the configuration in FIG. 18, elongate shaft 1800 includes guidewire lumen 1802 and an inflation lumen 1804 disposed adjacent to guidewire lumen 1802. In the configuration in FIG. 19, elongate shaft 1900 includes guidewire lumen 1902, inflation lumen 1904, and a control lumen 1906. It will be appreciated that the control lumens and inflation lumens herein can be used for many purposes, including, but not to be limited to, propulsion fluid flow, blood flow, cooling or heating fluid flow, delivery of a diagnostic or therapeutic agent, and the like. In the configuration in FIG. 20, elongate shaft 2000 includes guidewire lumen 2002, inflation lumen 2004, and two control lumens 2006 and 2008. In the configuration in FIG. 21, elongate shaft 2100 includes guidewire lumen 2102, inflation lumen 2104, and control lumens 2106. It will be appreciated that the elongate shafts herein can include additional configurations of guidewire lumen, inflation lumen, or control lumen. It will be further appreciated that in some embodiments there is no guidewire lumen.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A catheter system to induce fractures upon a vascular lesion, comprising:
    a catheter configured to advance to a vascular lesion location within a blood vessel, the catheter comprising:
        an elongate shaft wherein the elongate shaft defines at least a first orifice for fluid flow, wherein the elongate shaft further defines a propulsion fluid lumen; and
        an expandable balloon coupled to the elongate shaft and surrounding the first orifice;
    a propulsion system comprising an external fluid flow source in fluid communication with a proximal region of the propulsion fluid lumen, wherein the propulsion system is configured to propel a fluid from the first orifice toward a balloon wall; and
    an actuation valve at a distal region of the propulsion fluid lumen configured to create a pulsed fluid jet propelled from the first orifice.

2. The catheter system of claim 1, wherein the propulsion system is configured to propel the fluid toward the balloon wall at a velocity comprising a minimum of 1 meter per second (m/s), 5 m/s, or 10 m/s, wherein the velocity is measured where a fluid jet exits from the first orifice.

3. The catheter system of claim 1, wherein the elongate shaft defines at least two orifices, at least three orifices, or at least four orifices from which fluid is propelled within the balloon toward the balloon wall.

4. The catheter system of claim 3, wherein the orifices defined in the elongate shaft are spaced around a diameter of the elongate shaft, are spaced along a length of the elongate shaft, or both.

5. The catheter system of claim 1, wherein the actuation valve comprises an electromechanical valve and a control wire extending along the elongate shaft, or a rotary mechanical valve and a rotary control shaft extending along the elongate shaft.

6. The catheter system of claim 1, wherein the catheter system is configured to impart pressure to induce the fractures upon the vascular lesion within or adjacent a vessel wall of the blood vessel.

7. The catheter system of claim 1, wherein the expandable balloon is configured to expand from a collapsed configuration suitable for advancing the catheter through a patient's vasculature to a first expanded configuration suitable for anchoring the catheter in position relative to a treatment site.

8. The catheter system of claim 7, wherein the propulsion system is configured to propel the fluid from the first orifice toward the balloon wall when the balloon wall is in contact with a vessel wall and the balloon is maintained in the first expanded configuration.

9. The catheter system of claim 1, wherein the propulsion system is configured to propel the fluid from the first orifice toward the balloon wall to create an inertial impulse in a vessel wall to transfer momentum to the vascular lesion.

10. A method to induce fractures upon a vascular lesion, comprising:
- advancing a catheter to a vascular lesion location within a blood vessel, the catheter comprising a balloon coupled to an elongate shaft;
- expanding the balloon to a first expanded configuration; and
- while maintaining the balloon in the first expanded configuration, propelling a fluid from a first orifice defined in the elongate shaft toward a balloon wall, wherein propelling the fluid further comprises operating an actuation valve located at a distal region of a propulsion fluid lumen defined in the elongate shaft to pulse the fluid and create a pulsed jet of fluid.

11. The method of claim 10, wherein expanding the balloon further comprises expanding the balloon from a collapsed configuration suitable for advancing the catheter through a patient's vasculature to the first expanded configuration suitable for anchoring the catheter in position relative to the vascular lesion location.

12. The method of claim 10, further comprising, after propelling the fluid, further inflating the balloon to a second further expanded configuration.

13. The method of claim 10, wherein propelling the fluid further comprises propelling the fluid toward the balloon wall at a velocity comprising a minimum of 1 meter per second (m/s), 5 m/s, or 10 m/s, wherein the velocity is measured where a fluid jet exits from the first orifice.

14. The method of claim 10, wherein the actuation valve is an electromechanical actuation valve and activating the actuation valve comprises applying a voltage to a control wire extending along the elongate shaft.

15. The method of claim 10, wherein propelling the fluid further comprises imparting pressure upon the vascular lesion to induce fractures in the vascular lesion.

16. A catheter system to induce fractures upon a vascular lesion, comprising:
- a catheter configured to advance to a vascular lesion location within a blood vessel, the catheter comprising:
  - an elongate shaft wherein the elongate shaft defines at least a first orifice and a second orifice for fluid flow, wherein the elongate shaft further defines a propulsion fluid lumen; and
  - an expandable balloon coupled to the elongate shaft and surrounding the first orifice and the second orifice; and
- a propulsion system comprising an external fluid flow source in fluid communication with a proximal end of the propulsion fluid lumen and an actuation valve at a distal end of the propulsion fluid lumen, wherein the propulsion system is configured to propel a pulsed jet of fluid propelled from the first orifice and from the second orifice toward a balloon wall.

17. The catheter system of claim 16, wherein the pulsed jet of fluid is propelled toward the balloon wall at a velocity comprising a minimum of 1 meters per second (m/s), 5 m/s, or 10 m/s wherein the velocity is measured where a fluid jet exits from the first orifice.

18. The catheter system of claim 16, wherein the actuation valve comprises an electromechanical valve and a control wire extending along the elongate shaft, or a rotary mechanical valve and a rotary control shaft extending along the elongate shaft.

19. The catheter system of claim 16, wherein the first orifice and the second orifice are spaced from each other circumferentially.

20. The catheter system of claim 16, wherein the expandable balloon is configured to expand from a collapsed configuration suitable for advancing the catheter through a patient's vasculature to a first expanded configuration suitable for anchoring the catheter in position relative to a treatment site.

* * * * *